United States Patent [19]
Martin et al.

[11] Patent Number: 5,005,774
[45] Date of Patent: Apr. 9, 1991

[54] RAPID, SINGLE KERNEL GRAIN CHARACTERIZATION SYSTEM

[75] Inventors: Charles R. Martin; Robert Rousser; Daniel L. Brabec, all of Manhattan, Kans.

[73] Assignee: The United States of America as represented by the Secretary of Agriculture, Washington, D.C.

[21] Appl. No.: 519,196

[22] Filed: May 3, 1990

[51] Int. Cl.$^5$ ................................................ B02C 9/00
[52] U.S. Cl. ..................................... 241/101.2; 73/78; 221/211; 241/198 A; 241/222; 241/266
[58] Field of Search .................... 221/211; 73/78, 81, 73/83; 241/6–11, 37, 33, 101.2, 198 A, 101.3, 264, 266, 222

[56] References Cited

U.S. PATENT DOCUMENTS

| | | | |
|---|---|---|---|
| 1,481,632 | 1/1924 | Tatum | 241/198 A X |
| 2,484,228 | 10/1949 | Isay | 241/198 A |
| 2,839,917 | 6/1958 | Webster | 73/81 |
| 4,703,647 | 11/1987 | Eckhoff et al. | 73/81 |

FOREIGN PATENT DOCUMENTS

| | | | |
|---|---|---|---|
| 729228 | 7/1932 | France | 241/198 A |
| 1357071 | 12/1987 | U.S.S.R. | 241/198 A |

OTHER PUBLICATIONS

Y. Pomeranz et al., "Wheat Hardness Determined by a Single Kernel Compression Instrument with Semiautomated Feeder," Cereal Chem. 65(2): 86–94 (1988).

F. S. Lai et al., "Determination of Hardness in Wheat Mixtures, II; Apparatus for Automated Measurement of Hardness of Single Kernels," Cereal Chem. 62(3): 178–84 (1985).

*Primary Examiner*—Mark Rosenbaum
*Attorney, Agent, or Firm*—M. Howard Silverstein; John D. Fado; Curtis P. Ribando

[57] ABSTRACT

An automated grain characterization system includes grain crushing apparatus; a means for singulating kernels of grain and feeding them into the crushing apparatus; a means for measuring kernel size; a circuit for measuring kernel conductance; and a data acquisition and analysis subsystem for correlating crushing force, size, and conductivity to grain hardness. The output is a profile of the grain characteristics which can be compared to reference samples. This system is especially useful for grading and classifying wheat and predicting its end-use functional properties.

8 Claims, 8 Drawing Sheets

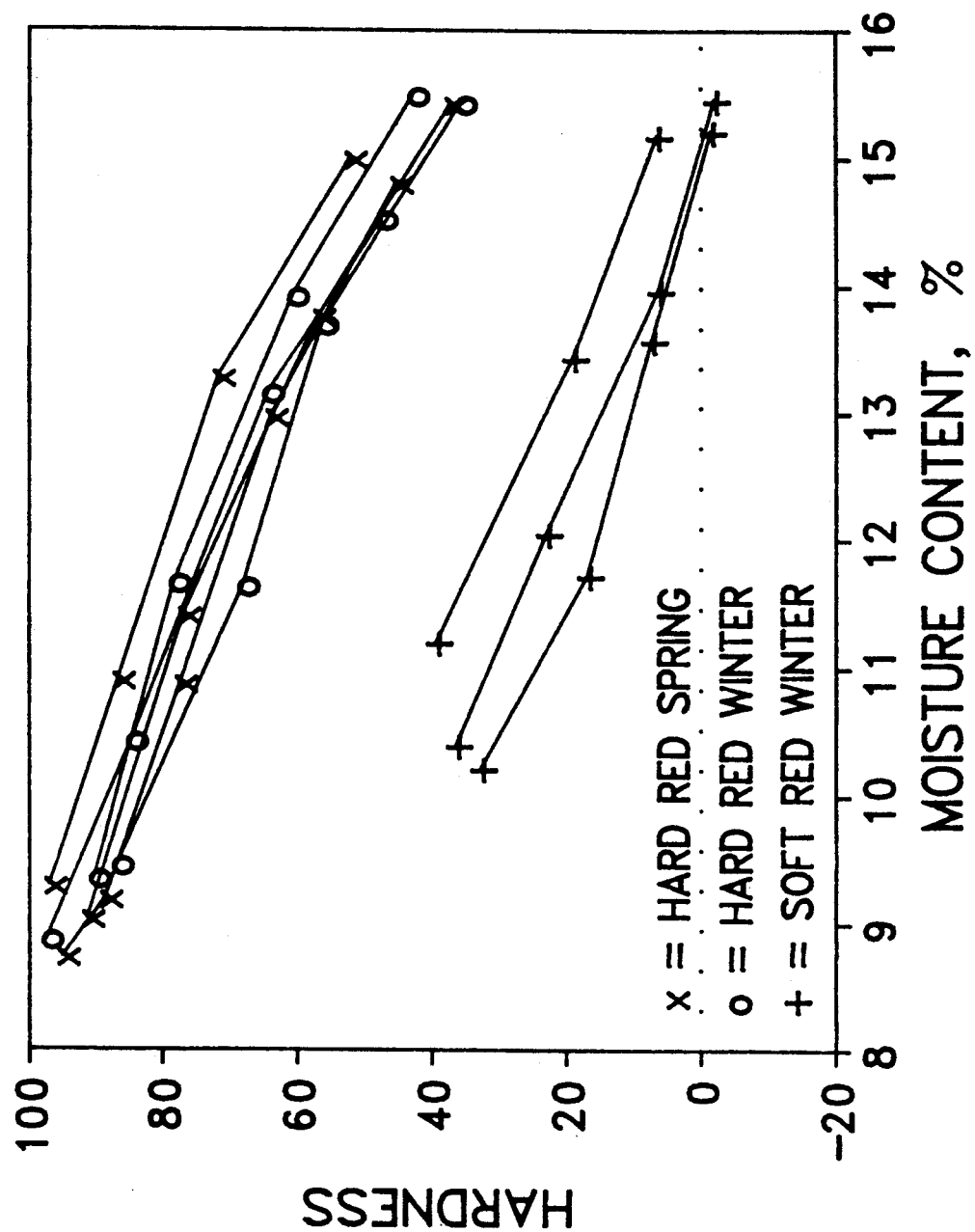

RAPID, SINGLE KERNEL GRAIN CHARACTERIZATION SYSTEM

CROSS-REFERENCE TO RELATED APPLICATION

This invention is related to commonly assigned application P.C. No. 2006.90 of Martin et al. entitled "Device for Singulating Particles," Ser. No. 07/519195, filed concurrently herewith on May 3, 1990.

BACKGROUND OF THE INVENTION

1. Field of the Invention

Hard and soft wheats require different milling procedures, and each class has acquired its own specific marketing niche based upon its end-use characteristics. Knowing the wheat class is important to the milling operation and for formulating appropriate marketing strategies. Present methods for classifying wheat as hard or soft are based upon color, shape, and other visual grain characteristics traditionally associated with the type. With the introduction of newer varieties, correlation between visual and end-use characteristics is not so distinct.

Bulk hardness measurements have been used as one approach to classifying wheat samples as hard or soft. However, bulk hardness measurements do not provide information as to whether or not wheats of different hardness have been mixed. Without a means for estimating product uniformity, grade determinations are difficult.

This invention relates to an apparatus and method useful for evaluating individual kernels of grain for hardness, and optionally for moisture content and grain size. The apparatus and method permit accurate classification and quality grading of grain without strict reliance upon its visual characteristics. The invention would be especially useful to grain inspectors of the Federal Grain Inspection Service (FGIS) for the grading of wheat and also for the purpose of assessing variability of hardness within a sample.

2. Description of the Prior Art

The current industry standard for determining wheat hardness is the American Association of Cereal Chemists (AACC) Method 39-70 (1983) employing near-infrared reflectance (NIR). In accord with this method, the NIR of sample wheat is compared to that of a series of reference wheats available through FGIS. Though this method effectively discriminates one class of wheat from another, the NIR instrumentation does not detect mixtures of different wheat classes.

Lai et al. [Cereal Chem. 62 (3): 178–184 (1985)] report the use of various attachments for the "Instron Universal Testing Machine" for performing compression, shear, and puncture tests on wheat samples and correlating the results with wheat hardness. Lai et al. also show a continuous automated single-kernel hardness tester referred to as the CASK-HAT. The principle of this instrument is to measure compression forces (stress) as a function of time. The device employs an in-stream pressure transducer to generate the compression force profile resulting from crushing a wheat kernel between a cam-actuated rod and a rigid anvil.

Pomeranz et al. [Cereal Chem. 65 (2): 86–94 (1988)] show a single kernel compression instrument with a semiautomated feeder for determining wheat hardness. This device was designed to crush individual kernels between two flat surfaces. The lower crushing surface is cam-driven, and the upper surface is connected to a load cell for generating data related to kernel thickness, kernel size, kernel deformation, and force to deform the kernel. The semiautomated feeder system orients each kernel with the crease downward by sliding it over action surfaces. The feeder centers the kernel under the load cell while simultaneously brushing the previously crushed kernel from the crushing surface.

Eckhoff et al., U.S. Pat. No. 4,703,647, disclose a grain hardness tester which feeds single grains into openings of a rotating plate, wherein the grains are sheared by a disc associated with a load cell and microprocessor. The microprocessor outputs a shear pattern indicative of the grain hardness.

SUMMARY OF THE INVENTION

We have now invented a system for characterizing cereal grains in terms of hardness, and optionally in terms of moisture content and grain size. The system includes a grain crushing device which comprises a driven rotor having a coarse outer surface which is in close proximity to a crescent-shaped inner surface (crescent) on a pivoting arm. The relative curvatures of the respective surfaces are such that they form a tapered gap having a wide end for feeding in singulated kernels of grain and a narrow end substantially less than the thickness of the grains for discharging crushed grain residues. A load cell or the like is provided for measuring the movement of the pivoting arm with time as a function of the physical resistance exerted by the grain on the crescent. This movement is correlated to a value indicative of grain hardness. The arm movement can also be correlated to grain size. Moisture content is determined as a function of conductance measured across the singulated kernel as it passes through the gap between the rotor and crescent.

In accordance with this discovery, it is an object of the invention to provide an automated system for rapidly and reliably characterizing cereal grain as to hardness, moisture content, and grain size.

It is a particular object of the invention to provide a system for characterizing the hardness of wheat for the purpose of classifying it as hard or soft.

It is also an object of this invention to provide a system which will detect blends of wheat classes in a bulk sample.

Another object of the invention is to provide an analytical tool useful in the sampling of bulk grain for the purpose of predicting its end-use functional properties.

Other objects and advantages of the invention will become readily apparent from the ensuing description.

BRIEF DESCRIPTION OF DRAWINGS

FIG. 10 is a graph of the hardness profiles determined by the system of the invention for two reference hard wheats and one reference soft wheat as a function of oven moisture content.

DETAILED DESCRIPTION OF THE INVENTION

Figure 8:
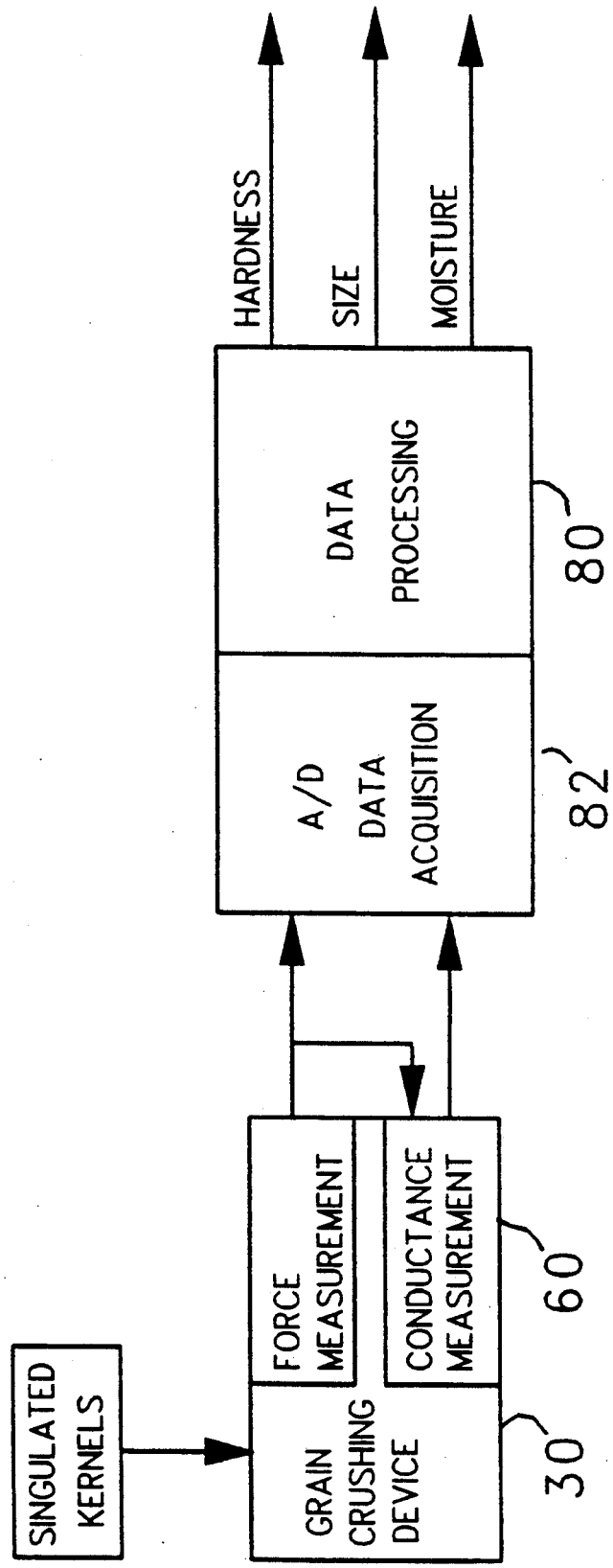
FIG. 8 is a schematic illustration of the complete single kernel grain characterization system.

Referring to FIG. 8, the principal components of the grain characterization system include the grain crushing device; a means for singulating kernels of grain and feeding them into the crushing apparatus; a means for measuring kernel size; a circuit for measuring conductance, and a data acquisition and analysis subsystem for correlating input relating to the grain crushing properties, and optionally the grain size and conductance, to grain hardness. The outputs are force and conductance profiles of the grain characteristics.

Figure 2:
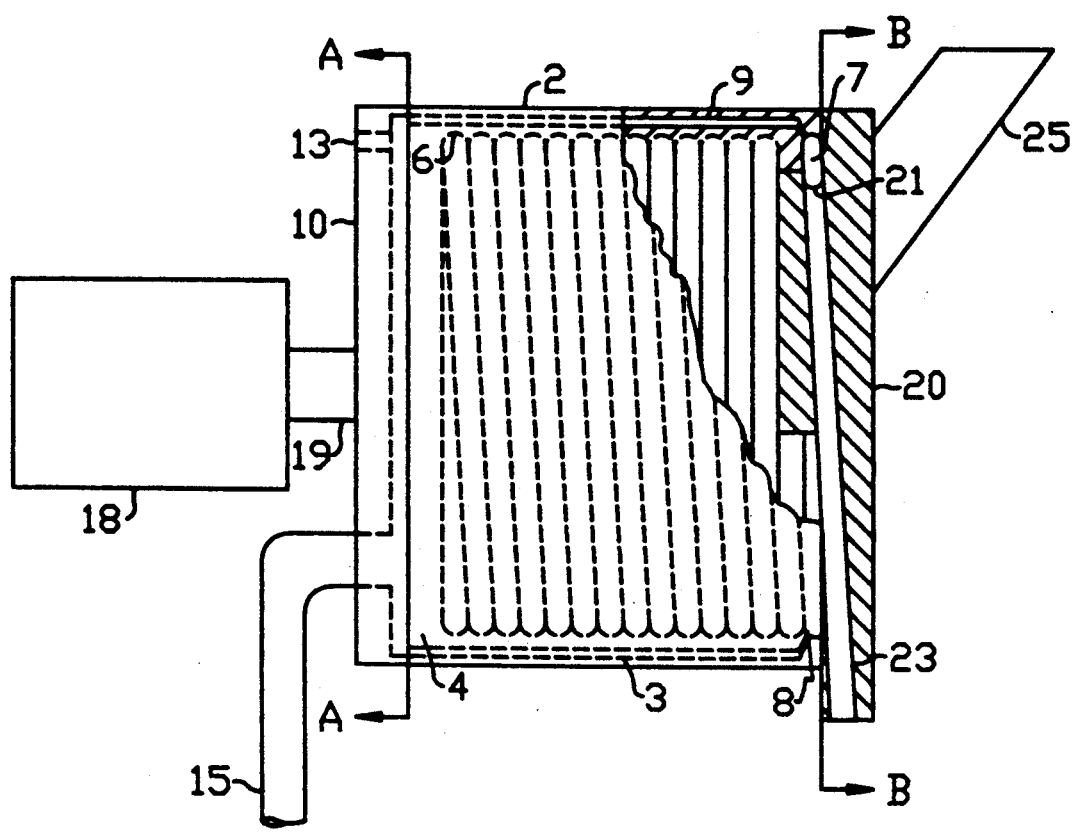
FIG. 2 is a partially cut-away front view of the feeder device.
Figure 3:
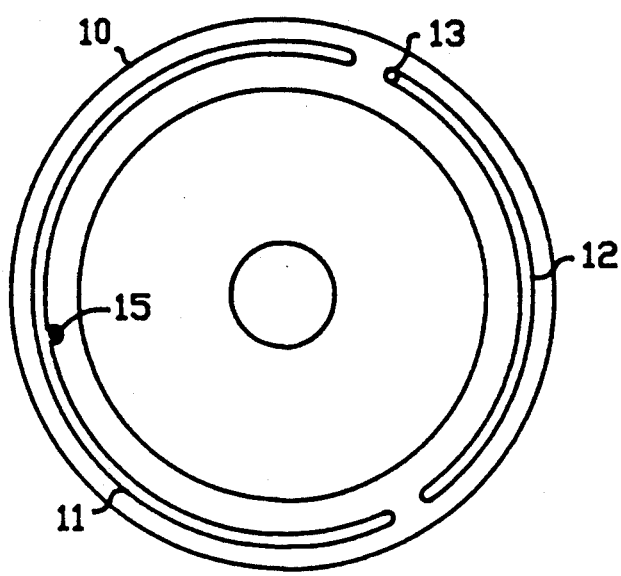
FIG. 3 is a sectional view along lines A—A of FIG. 2.
Figure 4:
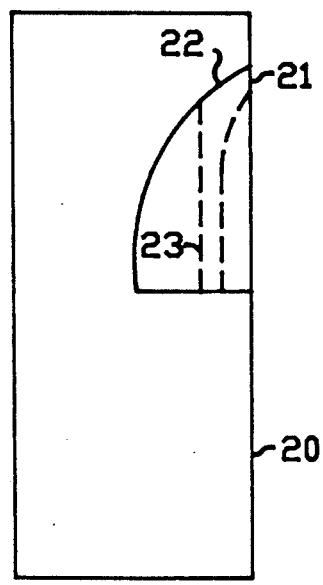
FIG. 4 is a sectional view along lines B—B of FIG. 2.

For rapid and efficient operation of the system, the preferred means for singulating and feeding kernels of the grain to be sampled into the crushing device is the feeder device 1 illustrated in FIGS. 2-4. This device takes advantage of the generally spheroid or ellipsoid shapes of cereal grains as well as their smooth surface which enables formation of a vacuum seal with the device as described in further detail below.

Figure 1:
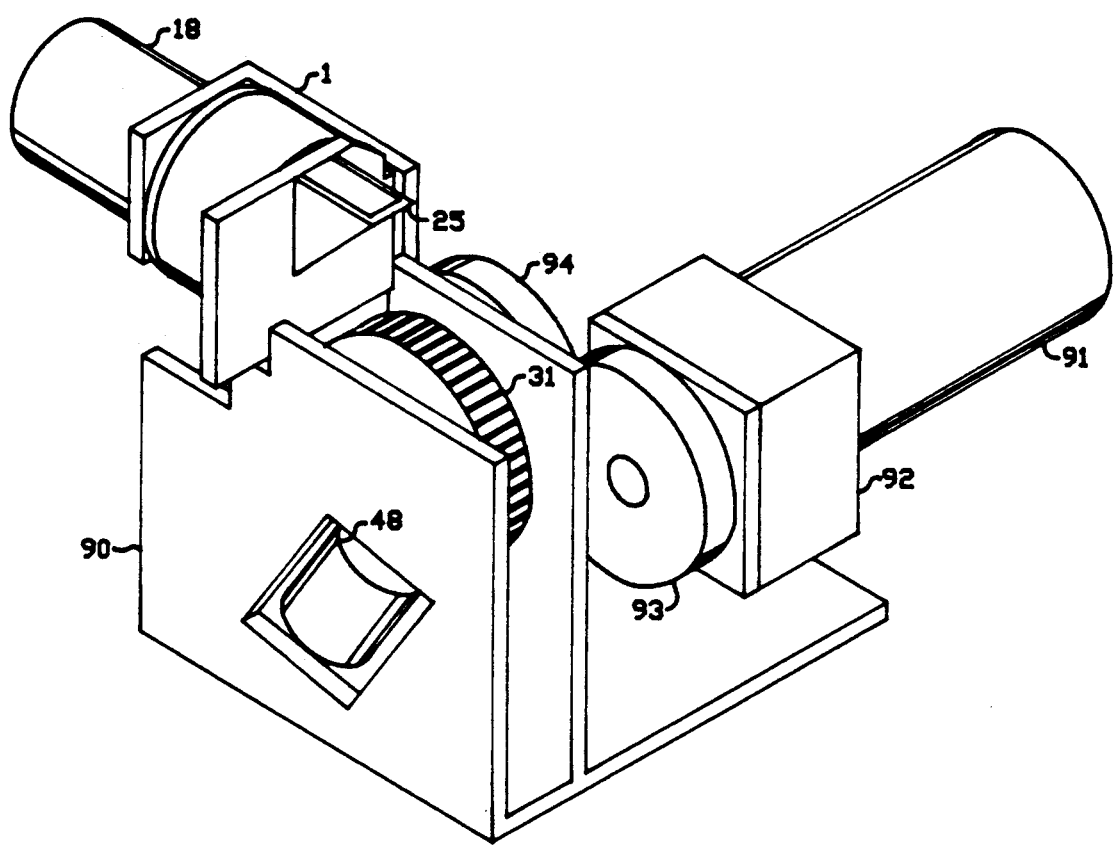
FIG. 1 is a perspective view of the single kernel grain characterization apparatus.

Referring to FIGS. 1 and 2, the feeder device is mounted on frame 90 and essentially comprises a drum 2 having cylindrical side wall 3, base 4, fixed face plate 20, and fixed base plate 10. The axis of the drum is oriented horizontally, and the drum is driven by motor 18 about the horizontal axis. Motor shaft 19 extends through the center of fixed base plate 10 which is rigidly mounted with respect to the motor so that the mating surfaces of base 4 and plate 10 have a very close tolerance. Hopper 25 is provided to charge the drum with the grain to be singulated.

A portion of the inner surface of side wall 3 is cut with a spiral groove 6 which terminates with concentric groove 7 near face plate 20. For best results, the cross-section of grooves 6 and 7 is U-shaped, and the transverse dimension should approximate that of the grain. Biaxially symmetrical kernels such as wheat and rice will thereby tend to become oriented longitudinally within the grooves. Spiral groove 6 preferably extends along the full length of inner surface so that all material which is charged into the drum via hopper 25 will ultimately be conveyed to concentric groove 7. It is understood that the direction of drum rotation is selected to promote advancement of the grain toward the concentric groove.

Concentric groove 7 is provided with one or more orifices 8 which are appropriately sized relative to the material to be singulated as described in further detail below. If a plurality of orifices are provided, they may be evenly spaced about the circumference of groove 7 so that the singulated kernels will be fed out by the device at regular intervals. Each orifice is in communication with a drilling 9 which extends through side wall 3 and base 4.

As best shown in FIG. 3, base plate 10 houses the means for valving a vacuum to drillings 9. In a preferred design, channel 11 connected to a vacuum source 15 is configured to communicate with each orifice 8 as it rotates in a circular path from some first predetermined point below the drum axis to some second predetermined point above the drum axis. Channel 12 communicates with the ambient or some positive pressure source through port 13. Channel 12 is preferably configured to communicate with each orifice 8 as it rotates from a third predetermined point above the drum axis to a fourth predetermined point intermediate to the third and first points. Thus, as drum 2 rotates, vacuum is alternately valved ON and OFF to drillings 9 and orifices 8. A grease seal or other tight-fitting arrangement between base 4 and base plate 10 is necessary to insure the appropriate pressure at the orifice at any given time.

In operation, the grain to be singulated is charged into drum 2 through hopper 25. The amount of the grain should fill no more than about 10-20% of the drum volume. As the drum rotates, kernels become aligned within the spiral groove 6 and are conveyed to concentric groove 7. The force of gravity tends to keep the grain near the bottom of the drum. When an orifice under vacuum sweeps under a kernel in groove 7, suction forces secure the kernel over the orifice. The kernel is thereby retained over the orifice as it rotates above the axis of the rotating drum, whereas other kernels of grain within the groove remain near the bottom. As drilling 9 comes into communication with channel 12, the vacuum is broken, and the grain is released.

The particle released from the orifice in the concentric groove is delivered to the next stage of processing or to its final destination by means of a guide. The guide may assume any of a variety of configurations. The embodiment shown in FIGS. 2 and 4 is specifically designed to maintain the orientation of a substantially biaxially symmetrical kernel of grain. Face plate 20 is provided with opening 21 to arcuate channel 22. The opening is positioned in close proximity to the point of release of the kernel from the orifice 8 and is in approximately the same plane as concentric groove 7. Arcuate channel 22 has a curvature which approximates the natural trajectory of the released kernel resulting from the momentum imparted by the drum as affected by the force of gravity. As the horizontal component of the trajectory becomes insignificant with respect to the vertical component, the kernel is then easily diverted to a different plane of descent, such as by the linear channel 23 shown in FIGS. 2 and 4.

By virtue of a constant speed of rotation of drum 2 and a constant spacing between orifices 8, the device can very precisely meter the singulated kernels at regularly spaced intervals. In tests with kernels of wheat, up to 200 kernels per minute have been singulated. Selection of the groove size, orifice size, vacuum pressure, and rate of drum rotation according to the particular application would be within the skill of a person in the art.

Figure 5:
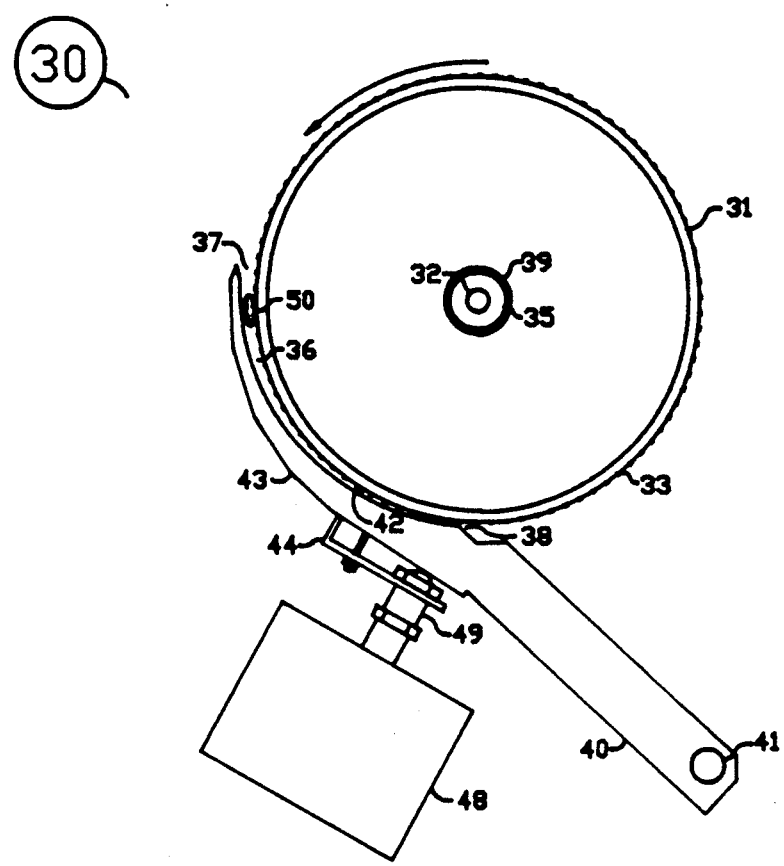
FIG. 5 is a side view of the rotor and pivoting arm for crushing the singulated grain samples.

As illustrated in FIG. 5., the crushing components of the device 30 comprise rotor 31 and pivoting arm 40. Referring also to FIG. 1, the rotor is fixed to shaft 32 which in turn is journaled to frame 90 by means of a bearing 35 on each side of the rotor. The bearings are electrically insulated from the frame by means of non-conductive sleeves 39. The rotor is driven by motor 91 through gear box 92 and transfer gears 93 and 94. Optionally, an electronic speed controller may be used to control the motor speed. Gear 94 is constructed of non-conductive material so as to cooperate with insulated bearings 35 for the purpose of electrically insulating the rotor from the rest of the system.

The outer surface 33 of the rotor is constructed of brass or other durable material and is textured to provide a gripping surface for the grain. In a preferred embodiment of the invention, the texture is provided by teeth as shown in detail in FIG. 6. The height of each tooth 34 should bear a ratio to the transverse dimension 51 of the grain kernel 50 in the range of about 0.05:1 to 0.5:1. The spacing between the teeth should bear a ratio to the longitudinal dimension 52 of the grain kernel in the range of about 0.1:1 to 0.8:1, and preferably 0.6:1 to 0.8:1. A functional advantage is obtained by shaping the teeth so that the leading edges are radial, and the trailing edges are oriented at approximately 15°–25° relative to the leading edges. This design permits the kernels to be gripped with little or no slippage, and fractured residues are readily released from the textured surface 33.

Pivoting arm 40 is secured to frame 90 at pivot point 41. Crescent-shaped inner surface 42, hereafter referred to as the crescent, has a curvature slightly greater than that of rotor 31. Inner surface 42 is smooth and is positioned relative to textured surface 33 so that a tapering, wedge-shaped gap 36 is formed therebetween. The relatively wide, feed end 37 of the gap is distal to the pivot point; whereas the relatively narrow, discharge end 38 of the gap is proximal to the pivot point. In its resting position, arm 40 is biased against reciprocating arm 49 by means of clamp 44 or some other suitable device. The taper of the gap should be such that the averaged-sized kernel of the grain sample to be tested makes contact with both the textured rotor surface 33 and the crescent 42 upstream of the midpoint of the gap. Thereafter, the gap should narrow sufficiently to insure that the kernel becomes substantially fractured or crushed prior to exiting at discharge end 38.

Mounted on frame 90 is a transducer 48 having reciprocating arm 49 in contact with the underside 43 of arm 40 when arm 40 is in its resting position. The transducer measures a force vector related to the fracturing of the kernel by generating a signal proportional to the deflection of the arm 40 (and also arm 49). The arm deflection is, in turn, a function of the resistive forces imparted by the grain on the opposing surfaces 33 and 42. It can be appreciated that, as the kernel first makes contact with both of the opposing surfaces, it deflects pivoting arm 40 away from rotor 31. As the kernel advances through the gap, the deflection increases until the compressive forces exerted on the kernel by the opposing surfaces cause it to fracture, resulting in a temporary relaxation of the pivoting arm. This iterative process continues as the kernel and its crushed pieces pass through the gap to discharge end 38.

The grain crushings discharged from end 38 are collected in a tray or suitable chamber (not shown) positioned below the rotor and pivoting arm assembly. Dust may be controlled by a fan (not shown) creating negative pressure inside the device. Air flowing through gap 36 not only controls the path of air-borne dust particles, but also cools the rotor and crescent.

Figure 7:
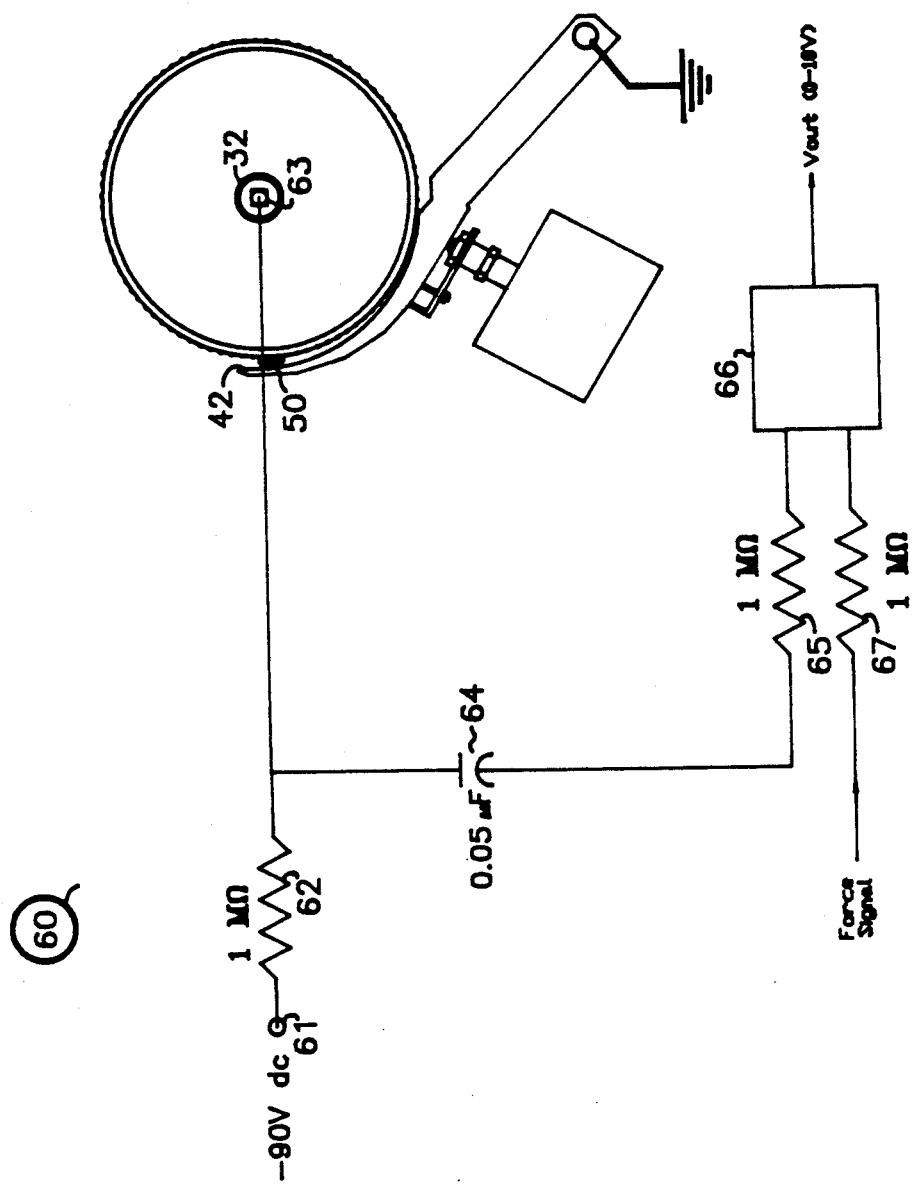
FIG. 7 is a schematic diagram of the conductance measurement circuit.

As shown in FIG. 7, conductance across kernel 50 is measured by a conductance circuit 60. This circuit applies a voltage from source 61 across resistor 62 to rotor shaft 32 by means of brush 63. When a kernel makes contact with both the rotor and the grounded crescent, continuity is established between the voltage source and ground. The magnitude of the resulting conductance signal is a function of the moisture content of the grain kernel. In the embodiment illustrated in FIG. 7, the signal is coupled through a capacitor 64 and resistor 65 to logarithmic ratio amplifier 66. Also input into amplifier 66 is the force signal applied through resistor 67 from transducer 48. The output signal is proportional to the logarithm of the conductance minus the logarithm of the force, or logarithm of conductance/force.

The signals relating to force and kernel size (described below) from transducer 48 and signals relating to conductance from amplifier 66 are inputted to an analog to digital (A/D) converter 82 in the data acquisition and analysis device 80 for further processing (FIG. 8). Suitable for this purpose would be any computer and appropriate software which will acquire, process, and store digitized data.

Data collected from a test sample kernel represent a force profile which is compared to a similarly generated force profile for reference samples of grain having known characteristics. Also, by calibrating the system for moisture levels using samples of known moisture content, moisture determinations for the test samples are readily obtained. Moisture calibration data are also useful for determining the effect of moisture on hardness parameters and to establish moisture correction constants for hardness values.

The diameter of a kernel determines the point in the cavity where initial contact is made between the crescent and the rotor surface. Large kernels make contact sooner and pass through a greater contact arc than small kernels. For constant rotor speed and zero slip between the rotor and kernel, the contact arc is proportional to contact time; the contact time is, in turn, proportional to kernel size. Thus, signals from transducer 48 can also be used as input to analysis device 80 for the determination of kernel size. Data relating to kernel size is useful in the grading of grain. In addition, a statistical size calibration is useful for making hardness measurement corrections relating to the kernel size of the test sample.

Though the device described herein was specifically designed for the characterization of wheat, it is envisioned that it would be equally useful for the characterization of any of the cereal grains, including rice, barley, corn, oats, sorghum, and the like. It is further envisioned that the invention would be applicable to the characterization of noncereal seeds, particularly those which have shape and hardness properties similar to those of wheat. The invention may also find application for determining certain properties of other industrial compounds or materials.

The following examples are intended only to further illustrate the invention and are not intended to limit the scope of the invention, which is defined by the claims.

EXAMPLE 1

A grain characterization system was assembled at the U.S. Grain Marketing Laboratory in Manhattan, Kans., specifically for the purpose of characterizing wheat according to kernel hardness, size, and moisture content. This experimental system is referred to as "ROLL2."

Single Kernel Feeder

A precision kernel feeder substantially as shown in FIGS. 2–4 was designed to deliver individual kernels to the crushing device from a bulk sample fed into the horizontal drum 1 (8.5 cm diam. by 5 cm) that rotates at 30 rpm. The concentric groove 7 is equipped with six evenly spaced orifices 8 which communicate with the vacuum valve mechanism.

Crushing Device

Figure 6:
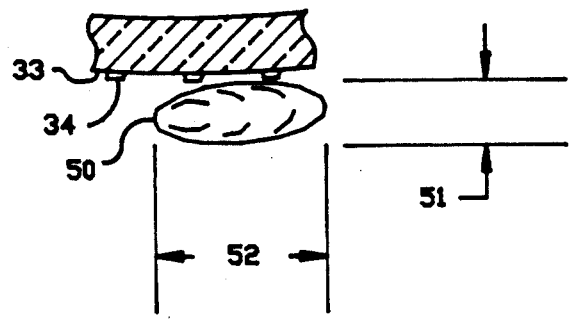
FIG. 6 is a detailed view of a preferred embodiment of the rotor surface.

The crushing device was constructed substantially as shown in FIGS. 1, 5, and 6. A 127-mm brass rotor 31 is equipped with teeth 0.38 mm high, 0.89 mm wide at the base with a 20° trailing edge taper, and spaced 3.54 mm apart. The rotor is driven by a 0.186 kW direct current gear motor using an electronic speed controller.

A stainless steel pivoting arm 40 is a lever design with a two to one mechanical advantage between the point of most frequent kernel contact and the point of kernel exit. This design mechanically amplifies initial contact force for the purpose of enhanced signal detection and increased sensitivity at the initial fracture stage.

The pivoting arm is supported by a linear variable differential transformer load cell 47 (Daytronic 152A-100, 100 lb rated load range) connected to an excitation and signal conditioning circuit (Schaevitz LPM-210). The calibration setting for the load cell is 108.3N (neutons) per volt which translates to an A/D converter (12 bit resolution 10 v full scale) output of 0.2644N per A/D count.

The rotor-crescent gap 35 is a nonlinear wedge design with a 4.370-mm gap (to accept large white and durum kernels) at the entrance. The gap decreases through a 93° crescent arc to 0.508 mm at the exit (measurements are tooth tip to crescent). With the rotor operated at 120 rpm, kernels are deformed at a rate of approximately 30 mm/s.

The byproducts generated during kernel crushing, heat from friction on the crescent, and dust from crushed kernels are controlled by air flow. A fan (60 cfm) creates a negative pressure inside the machine that moves air to cool the crescent and control the path of air-borne dust particles.

Conductance Circuit

A regulated −90 v dc source (Analog Modules model 521, Longwood, Fla.) is connected to the rotor through a 1 megohm resistor. The conductance signal, which ranges between 0.002 and 2.0 micro-Siemens for single kernels ranging in moisture between 10 and 17% respectively, is coupled through a 0.05 microfarad capacitor to a logarithm ratio amplifier which provides an output signal proportional to logarithm (conductance)-logarithm (force) or logarithm (conductance/force). The output signal, 1.5–8.5 v, is inputted to the A/D converter.

Data Acquisition

A multifunction high-speed analog/digital I/O expansion board (MetraByte Dash-16) mounted in an expansion slot of an IBM PC/AT compatible personal computer is used for data acquisition. The data acquisition cycle begins with the A/D system monitoring the force signal to detect kernel entry. Upon kernel entry detection, the system initiates rapid acquisition of conductance to force ratio data and also force data at 0.25 ms intervals and stores the data representing two profiles in computer memory. Data acquisition continues for 125 ms with actual crushing time ranging between 50 and 100 ms. At a kernel throughput rate of three per second, 208 ms of CPU time is available for data processing, storing, and initializing of the system for the next kernel.

Machine Data Summary Parameters

The single kernel crushing system generates a total of 1000 individual measurements for each kernel processed. Individual kernel measurements were condensed to a small number of summary parameters. As a starting point for Roll2 evalution, an initial data set was collected for samples of soft and hard wheats at about 12.5% moisture content. Slope values (DY), measured in A/D counts across the 0.25 ms interval, were calculated from the data representing the force profile. A frequency distribution of the DY counts was made to determine the relationship between sample hardness and DY values.

Since soft wheats mill into a larger number of smaller particles than hard wheats, it was postulated that the number of the positive slopes across the digitized interval in a force profile may be proportional to the number of particles, and that the slope value may be proportional to the size of particles created by crushing. This postulation permitted the development of a hardness measurement based on the positive slope values from the digitized force-time profile. From the initial data set, 13 machine data summary parameters were selected as a data base for kernels processed by the Roll2 system. After calibration for moisture and size, the machine data summary parameters were reduced to those shown in Table I.

Crushing Profiles

Soft wheats produce smooth low profiles with "flowing" or mild slopes as kernels disintegrate into a multitude of small particles. Hard wheats produce jagged profiles with multiple peaks and sharper slopes as kernels fracture into smaller and smaller particles.

The frequency distribution of the DY counts shows that soft kernels have more DY counts between 1 and 8 than hard kernels, whereas hard kernels have more DY counts greater than 8 than do soft kernels. In Roll2, a DY count of 8 translates to about 275N per mm at the 30 mm/s deformation rate.

TABLE I.

| No. | Definition | Projected relationship |
|---|---|---|
| 1 | moisture signal, A/D count | A parameter related to moisture; logarithm of the conductance to force ratio. |
| 2 | peak force, A/D count | Used to select the data points for determining moisture measurement. |
| 3 | number of DY > 0 | A parameter related to size based on the time a kernel exerts force on the crescent. |
| 4 | sum of 1/DY, for all DY > 0, A/D count | A parameter that is proportional to hardness. Soft wheat kernels produce a large value; hard kernels produce a small value. |
| 5 | number of DY > 8 | A parameter that is proportional to hardness. |
| 6 | sum of DY for all DY > 0, A/D count | A parameter that is related to the work to crush a kernel. |

EXAMPLE 2

The grain characteristics system described in Example 1 was calibrated for measuring moisture, size, and hardness of wheat samples.

Moisture Calibration

Figure 9:
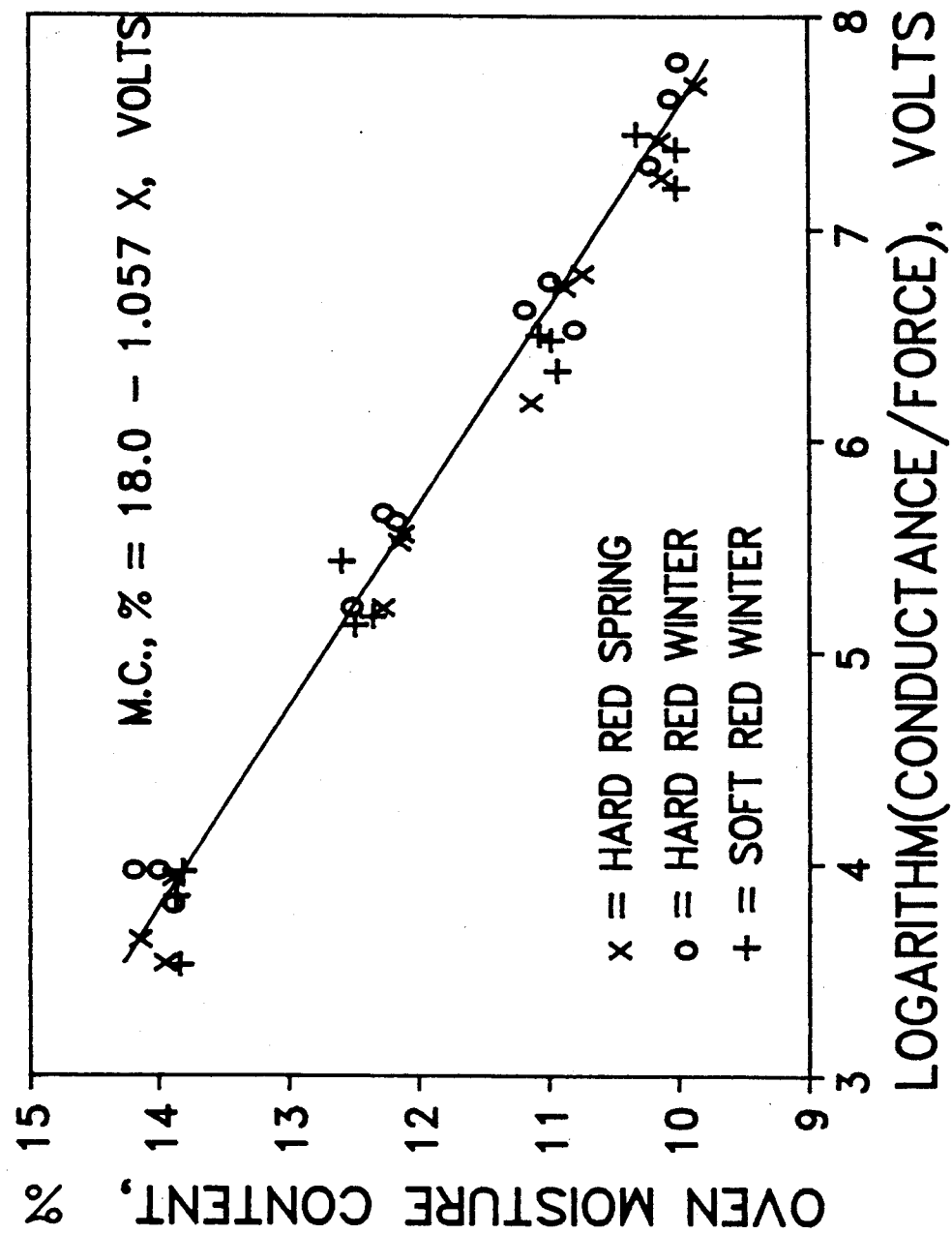
FIG. 9 shows the relationship between the oven moisture content of three test wheats and the logarithm of the conductance to force ratio in volts as determined by the system of the invention.

A moisture calibration was obtained using three varieties each of hard red spring (HRS), hard red winter (HRW), and soft red winter (SRW) wheats at five different moisture levels in the range between 10 and 17%. Moisture determinations for all wheats at each moisture level were made using the oven method for wheat ground in a Wiley mill through a #20 mesh screen. Moisture calibration data shown in FIG. 9 were used to determine the effect of moisture on hardness parameters and to establish moisture correction constants. The percent moisture content equals $18.0 - 1.057 \times$ logarithm (conductance/force). These results establish that one calibration was satisfactory for each of the wheat classes tested. Moisture determinations allow hardness measurements to be corrected to a constant moisture basis.

Conductance was found to be related to moisture, contact area, and force of the kernel as it was deformed and crushed between the rotor and crescent. Contact area and force change constantly during the kernel deformation process. As a result, the conductance signal is also changing even though the kernel may have uniform moisture content. Differences in kernel size, shape, orientation, and hardness also influence the force on the pivot arm. However, the ratio of conductance to load cell force was nearly constant when crushing equilibrated kernels.

From kernel to kernel, the most consistent moisture measurements were near the end of the force profile and generally corresponded to the region near the peak force value. All moisture determinations from Roll2 were calculated from the logarithm (conductivity/force) signal at or near the peak force value.

Size Calibration

A statistical size calibration was developed using the number of time intervals that a kernel exerts force on the pivot arm (number of positive DY values in force signal). A size algorithm, developed from 253 samples representing the five major wheat classes, was used for hardness measurement corrections relating to kernel size. Kernel size was determined by kernel weight of three different sizes segregated by sieving. Average kernel weight of each sieved fraction was determined before crushing. If the sieved fraction was less than 16 kernels, the fraction was omitted in the size calibration.

The contact time for smaller kernels was less than the contact time for larger kernels. The initial kernel contact may occur at rotor tooth tip, or at the base of a rotor tooth (land) which represents a dimensional difference of 0.38 mm. As deformation progresses, the kernel may slip off the tooth into the land or split into two pieces with each piece separated by a tooth. When splitting or slipping occur, the force exerted by the kernel on the crescent is momentarily reduced, which frequently produced negative DY values. Splitting and slipping introduce a random machine reaction to the size measurement using rotor-crescent contact time. Hard kernels were observed to require a slightly longer time to pass through the instrument than soft kernels of the same size. This may be the result of two effects: (1) that more slip occurs during hard than soft kernel crushing, and (2) that more rotational slowing of the rotor is related to greater torque requirement for crushing hard kernels than soft kernels.

Roll2 size measurements for the sieved size groups were highly correlated with average kernel weight ($r^2 = 0.916$, $N = 754$). However, the hardness interaction on the size measurement was apparent in that most of the points below the regression line were hard wheats, whereas most points above the line were soft wheats.

Hardness Calibration

Hardness was determined from the force profile stored in computer memory by the A/D converter. At the end of data acquisition from a kernel, the computer and processing software make a frequency summation of specific slope values measured across time intervals of the A/D converter (0.25 ms) and stores summary parameters in memory. After all kernels in a sample are crushed, the summary parameters are further processed by the computer and software to calculate hardness values corrected for moisture and size for each kernel.

Samples from an NWHS (National Wheat Hardness Survey) reference set of 17 wheat samples was used for hardness calibration and determination of the optimum size correction coefficients.

For Roll2 hardness calibration, the scaling constants (slope and intercept) were determined so that the five soft and ten hard wheat sample average hardness values were 25 and 75, respectively. Overlap between hard and soft wheat hardness values may be represented by the absolute difference of the hard and soft means divided by the sum of the hard and soft standard deviations. This ratio represents the number or multiple of standard deviations where overlap occurs between hard and soft wheat hardness values in a normal distribution and was used as an index of classing efficiency. The larger the index, the greater the classing efficiency, and an index value of three represents very little overlap.

Optimum size correction constants were determined by selecting the values that produce the greatest classing efficiency (least overlap) between soft and hard wheat varieties in the NWHS reference set. Selection was made after several iterative trials starting with no size correction and increasing the size correction until a maximum classing efficiency was observed.

A smoothing method which improves both the classing efficiency and stability of Roll2 was developed using two hardness functions in a strategy to reduce kernel to kernel variabilty. By selecting one of two hardness values for each kernel that was closest to the sample mean of both hardness values, the kernel to kernel variation was reduced. However, the distinction between hard and soft wheat was retained, because each hardness algorithm independently differentiated hard and soft wheat in nearly equal manner.

Roll2 hardness measurements were based on the summary parameter sum $1/DY > 0$ and a combination of the summary parameters $\#DY > 0$ and $\#DY > 8$. The sample averages of the two hardness functions were highly correlated ($r^2 = 0.97$, $N = 253$) across samples of the five major wheat classes: durum, HRS, HRW, winter wheat (WW), and SRW. The high correlation suggests that the two hardness algorithms measure similar kernel properties. Hardness values based on the sum $1/DY > 0$ parameter were corrected to a reference 12% moisture content and Roll2 kernel size value of 35 as follows:

$$H1 = b1 + a1 \times [\text{sum } 1/DY > 0 + (12 - MC) \times mc1 + (35 - SZ) \times sz1]$$

Hardness values based on #DY>0 and #DY>8 were corrected for moisture and size as follows:

$$H2 = b2 + a2 \times [100 \times \#DY>8/(-\#DY>0 \times SZ^{0.5}) + (12-MC)$$

$$\times mc2 + (35-SZ) \times sz2].$$

Where:
a = 50/(ave. HRW & HRS values − ave. SRW & WW values),
b = 75 − ave. HRW & HRS values × a,
MC = Roll2 moisture content, %,
SZ = Roll2 kernel size,
mc1 = 2.69 for sum 1/DY>0,
mc2 = 6.75 for #DY>8 function,
sz1 = 0.30 for sum 1/DY>0,
sz2 = 0.05 for #DY>8 function.

Using the scaling and moisture constants determined from a March calibration, single kernel hardness values were calculated for each sample in the NWHS reference set when the average moisture content of the set was 11.6, 12.3, and 13.3 percent in March, May, and July, respectively. The summary in Table II shows that Roll2 average hardness values of the HRS wheats were larger than the HRW wheats, the WW wheats were between the HRW and SRW wheats, and the SRW wheats were lower than the WW wheats.

EXAMPLE 3

Ten-gram samples of three HRS, three HRW, and three SRW varieties at 10, 11, 12.5, 14, and 17 percent moisture contents (oven method) were evaluated by the calibrated Roll2 system described in Examples 1 and 2. The results confirmed that the logarithm of the conductance/force ratio correlated closely with the oven moisture content and that one calibration would be acceptable for wheats of these different classes. The graphs of hardness vs moisture content in FIG. 10 establishes that the system is effective in discriminating classes of wheat over the full range of the moisture contents tested.

TABLE II.

Roll2 Hardness Values and Classing Efficiency for the NWHS Sample Set at Three Moisture Levels

| Sample set moisture, % av. | 300 Kernel av. hardness value | | | | | | Classing efficiency index |
|---|---|---|---|---|---|---|---|
| | Durum | HRS | HRW | WW | SRW | av.* | |
| 11.6 | 101.2 | 76.3 | 73.7 | 36.4 | 8.0 | 58.3 | 1.27 |
| 12.3 | 105.7 | 82.1 | 76.1 | 39.0 | 10.3 | 61.9 | 1.27 |
| 13.3 | 107.0 | 80.9 | 74.9 | 36.8 | 7.7 | 60.3 | 1.29 |

*Excluding durum.

It is understood that the foregoing detailed description is given merely by way of illustration and that modification and variations may be made therein without departing from the spirit and scope of the invention.

We claim:

1. An apparatus for characterizing cereal grains comprising:
   a rotor having a coarse outer surface;
   a means for driving said rotor;
   an arm having a pivot point and a crescent-shaped inner surface which has a curvature greater than that of the outer surface of said rotor, said arm being positioned relative to said rotor so that a tapered gap having a wide, feed end and a narrow, discharge end is formed between the outer surface of the rotor and the crescent-shaped inner surface, wherein the spacing between said surfaces at the narrow end is substantially less than the thickness of the grains;
   a means for feeding singulated kernels of grain into said gap;
   a means for measuring the movement of said arm with time about the pivot point as a function of the physical resistance exerted by the grain on the crescent-shaped inner surface; and
   a means for correlating said movement to a value indicative of grain hardness.

2. An apparatus as described in claim 1 wherein said coarse outer surface of the rotor comprises a plurality of teeth, each of which extends transversely across the width of the rotor and having a height sufficient to grip a singulated kernel, wherein the spacing between adjacent teeth is less than the length of the kernel.

3. An apparatus as described in claim 1 wherein said means for measuring is a transducer and is in contact with said arm at a point intermediate to the pivot point and the feed end.

4. An apparatus as described in claim 1 wherein said means for correlating comprises a computer software program which compares the crush profile of a test sample of said singulated kernels with the crush profile of one or more reference samples of singulated kernels.

5. An apparatus as described in claim 4 wherein said computer software program also correlates said movement to grain size.

6. An apparatus as described in claim 1 and further comprising a means for measuring the conductivity of said singulated kernel and correlating the conductivity to moisture content.

7. An apparatus as described in claim 6 wherein both the rotor and arm are electrically insulated, and the conductance across the kernel between the rotor and arm is measured.

8. An apparatus as described in claim 7 wherein said means for feeding singulated kernels into said gap comprises:
   a drum adapted to hold a plurality of the kernels and to rotate horizontally about its axis and having an inner surface and an outer surface, wherein the inner surface has a spiral groove extending at least a portion of the length of the inner surface and terminating in a concentric groove near one end of the drum;
   at least one orifice in the concentric groove having a dimension substantially smaller than one of the kernels;
   a means for applying a vacuum to the orifice during the time that the orifice rotates in a circular path from a first predetermined position which is below the axis of the drum to a second predetermined position which is above the first position, whereby a single kernel positioned over the orifice during the time the vacuum is applied will be retained over the orifice;
   means for releasing the vacuum when the orifice is positioned at a third predetermined position which is above the first position, whereby the single kernel will be released from the orifice;
   means for directing the released kernel to the gap.

* * * * *